US012708297B2

(12) United States Patent
Ogirko et al.

(10) Patent No.: US 12,708,297 B2
(45) Date of Patent: Aug. 18, 2026

(54) CONTINUOUS ELECTROCHEMICAL MONITORING

(71) Applicant: Cypress Semiconductor Corporation, San Jose, CA (US)

(72) Inventors: Roman Ogirko, Lviv (UA); Volodymyr Bihday, Lviv (UA); Igor Musiichuk, Lviv (UA); Yaroslav Berko, Zhovkva (UA); Richard Sweet, Jr., San Diego, CA (US)

(73) Assignee: Cypress Semiconductor Corporation, San Jose, CA (US)

( * ) Notice: Subject to any disclaimer, the term of this patent is extended or adjusted under 35 U.S.C. 154(b) by 869 days.

(21) Appl. No.: 18/075,093

(22) Filed: Dec. 5, 2022

(65) Prior Publication Data

US 2024/0180458 A1 Jun. 6, 2024

(51) Int. Cl.

| | |
|---|---|
| ***A61B 5/1473*** | (2006.01) |
| ***A61B 5/00*** | (2006.01) |
| ***A61B 5/145*** | (2006.01) |
| ***H03F 3/45*** | (2006.01) |

(52) U.S. Cl.

CPC .......... *A61B 5/1473* (2013.01); *A61B 5/0004* (2013.01); *A61B 5/0031* (2013.01); *A61B 5/14532* (2013.01); *H03F 3/45475* (2013.01); *H03F 2200/156* (2013.01); *H03F 2200/375* (2013.01); *H03F 2203/45151* (2013.01)

(58) Field of Classification Search

CPC . A61B 5/1473; A61B 5/0004; A61B 5/14532; A61B 5/7225; H03F 2200/156; H03F 2200/375; H03F 2203/45151

See application file for complete search history.

(56) References Cited

U.S. PATENT DOCUMENTS

| | | | | |
|---|---|---|---|---|
| 2008/0249385 A1* | 10/2008 | Phan | .................. | A61B 5/14532 600/347 |
| 2017/0273610 A1* | 9/2017 | Suri | .................. | A61B 5/15105 |

* cited by examiner

*Primary Examiner* — Christian Jang

(57) ABSTRACT

A continuous electrochemical monitoring device according to an example includes an electrochemical transducer to continually generate a signal indicative of a characteristic of a user. The device includes a transimpedance amplifier to receive the signal from the transducer at a first input, receive a bias voltage at a second input, and generate an output voltage. The device includes an operational amplifier to receive the output voltage at a first input, and output an amplified output voltage. The device includes a differential analog to digital converter to receive the amplified output voltage at a first input, receive the bias voltage at a second input, and continually generate a digital output indicative of the characteristic of the user.

20 Claims, 10 Drawing Sheets

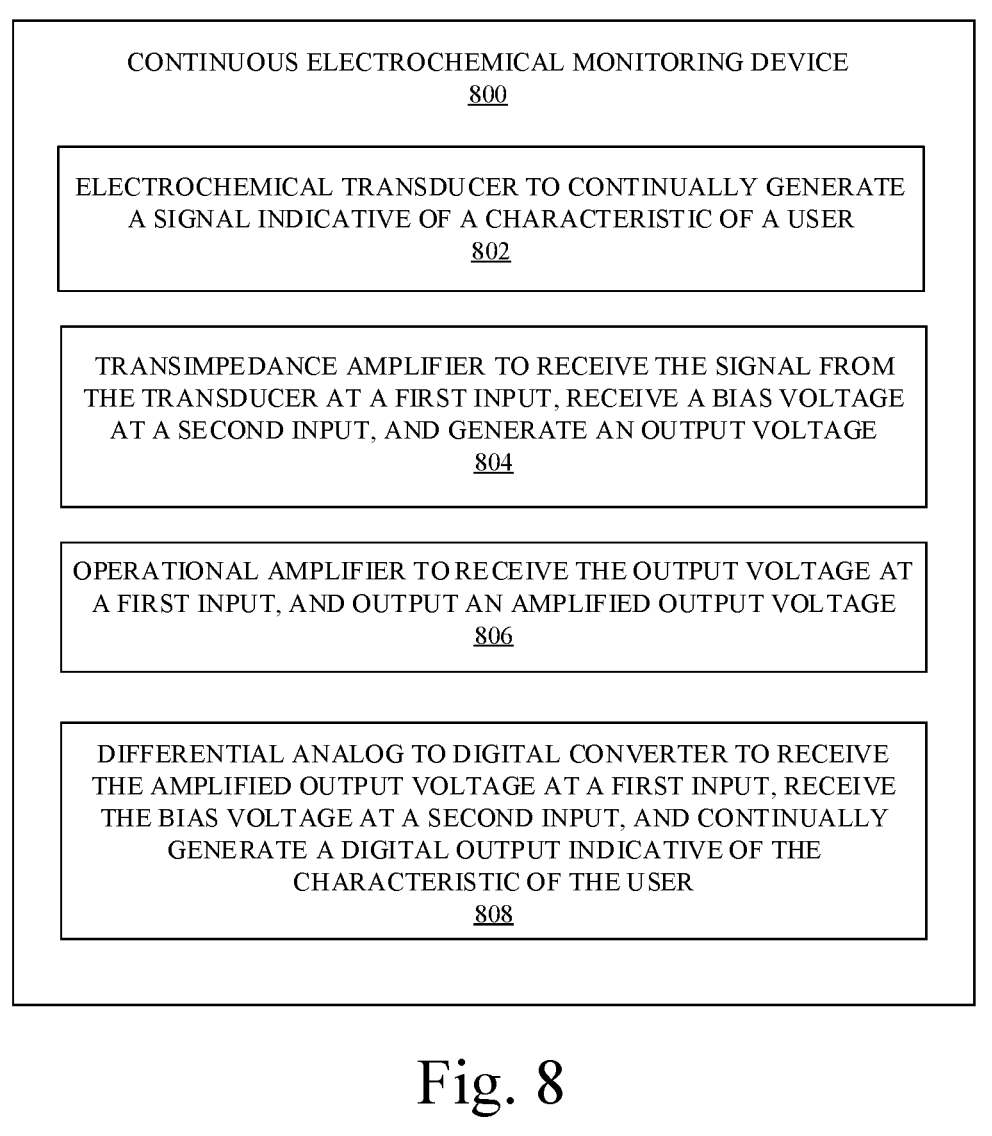

CONTINUOUS ELECTROCHEMICAL MONITORING DEVICE
800

ELECTROCHEMICAL TRANSDUCER TO CONTINUALLY GENERATE A SIGNAL INDICATIVE OF A CHARACTERISTIC OF A USER
802

TRANSIMPEDANCE AMPLIFIER TO RECEIVE THE SIGNAL FROM THE TRANSDUCER AT A FIRST INPUT, RECEIVE A BIAS VOLTAGE AT A SECOND INPUT, AND GENERATE AN OUTPUT VOLTAGE
804

OPERATIONAL AMPLIFIER TO RECEIVE THE OUTPUT VOLTAGE AT A FIRST INPUT, AND OUTPUT AN AMPLIFIED OUTPUT VOLTAGE
806

DIFFERENTIAL ANALOG TO DIGITAL CONVERTER TO RECEIVE THE AMPLIFIED OUTPUT VOLTAGE AT A FIRST INPUT, RECEIVE THE BIAS VOLTAGE AT A SECOND INPUT, AND CONTINUALLY GENERATE A DIGITAL OUTPUT INDICATIVE OF THE CHARACTERISTIC OF THE USER
808

Fig. 8

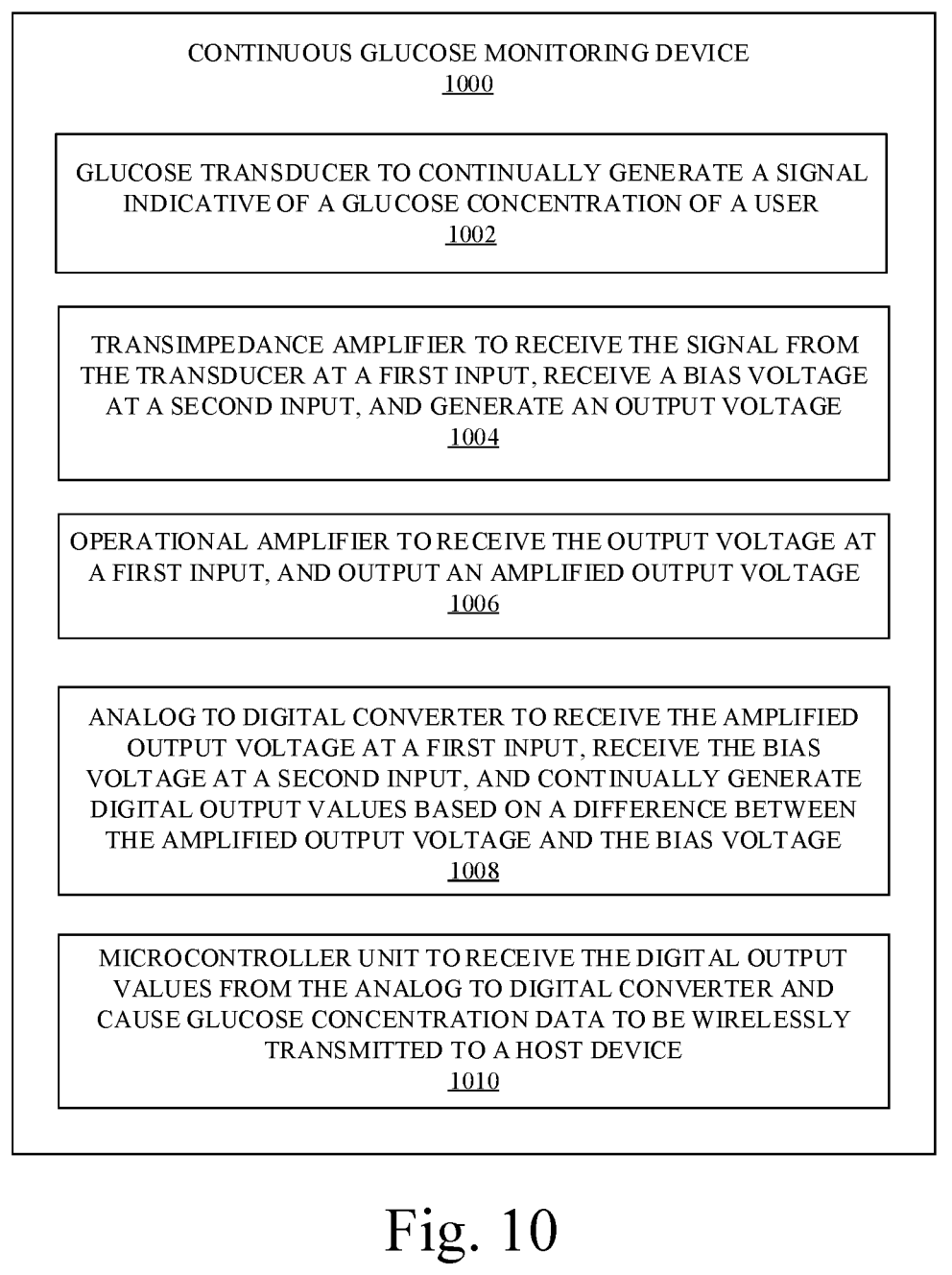

CONTINUOUS GLUCOSE MONITORING DEVICE
1000

GLUCOSE TRANSDUCER TO CONTINUALLY GENERATE A SIGNAL INDICATIVE OF A GLUCOSE CONCENTRATION OF A USER
1002

TRANSIMPEDANCE AMPLIFIER TO RECEIVE THE SIGNAL FROM THE TRANSDUCER AT A FIRST INPUT, RECEIVE A BIAS VOLTAGE AT A SECOND INPUT, AND GENERATE AN OUTPUT VOLTAGE
1004

OPERATIONAL AMPLIFIER TO RECEIVE THE OUTPUT VOLTAGE AT A FIRST INPUT, AND OUTPUT AN AMPLIFIED OUTPUT VOLTAGE
1006

ANALOG TO DIGITAL CONVERTER TO RECEIVE THE AMPLIFIED OUTPUT VOLTAGE AT A FIRST INPUT, RECEIVE THE BIAS VOLTAGE AT A SECOND INPUT, AND CONTINUALLY GENERATE DIGITAL OUTPUT VALUES BASED ON A DIFFERENCE BETWEEN THE AMPLIFIED OUTPUT VOLTAGE AND THE BIAS VOLTAGE
1008

MICROCONTROLLER UNIT TO RECEIVE THE DIGITAL OUTPUT VALUES FROM THE ANALOG TO DIGITAL CONVERTER AND CAUSE GLUCOSE CONCENTRATION DATA TO BE WIRELESSLY TRANSMITTED TO A HOST DEVICE
1010

Fig. 10

CONTINUOUS ELECTROCHEMICAL MONITORING

BACKGROUND

Parameter or characteristic measurement is involved in numerous fields, such as packaging, medical devices, human or pet health monitoring, home automation, food storage, and so on. Parameters can include biological, chemical, electrical, electrochemical, or any other appropriate parameter, such as temperature, humidity, or chemical changes for food safety, among others. For example, in one particular health monitoring related example, certain diabetes blood sugar monitors measure the amount of glucose in the blood of a user. Some parameter measurement and analysis methods may not make continuous measurements, which can lead to the loss of helpful information for analysis. Some parameter measurement and analysis methods may involve a wired or plugged-in connection from the sensor to the evaluating device, thus leading to additional complexity and difficulty of use.

For these and other reasons, a need exists for the present invention.

BRIEF DESCRIPTION OF THE DRAWINGS

FIG. 8 is a block diagram illustrating a continuous electrochemical monitoring device according to an example.

FIG. 10 is a block diagram illustrating a continuous glucose monitoring device according to an example.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Examples disclosed herein are directed to contactless sensing devices and systems that provide for detecting and transmitting electrochemical characteristics or parameters (e.g., glucose concentration). Other examples may involve detecting and transmitting one or more of biological, chemical, electrical, and other characteristics or parameters. Some of these examples are directed to a continuous glucose monitoring (CGM) device and system. In some CGM devices, measurement results may be influenced by amplifier offset voltages, and may depend on a digital-to-analog converter's (DAC's) voltage accuracy. The amplifier offset voltages may be an issue if current in nano-amps is being measured, and micro-volts offset of amplifiers in these CGM devices may be used to measure small current. Implementation of some measurement methods that use manipulation of the bias voltage may be complicated due to dependence of the result of measurement on the DAC's voltage.

Examples disclosed herein use a measurement method in which the output is proportional to the current of the transducer, even if manipulations are performed with the value of the bias voltage of the transducer. This expands the scope of applications not only for operation at DC bias. Some examples use a method of modulating the informative parameter against the background of big non-informative parameters to eliminate the influence of these non-informative parameters by further demodulation. The method may use manipulation of the value of the transmission coefficient for the measured current as a modulation procedure.

Figure 1:
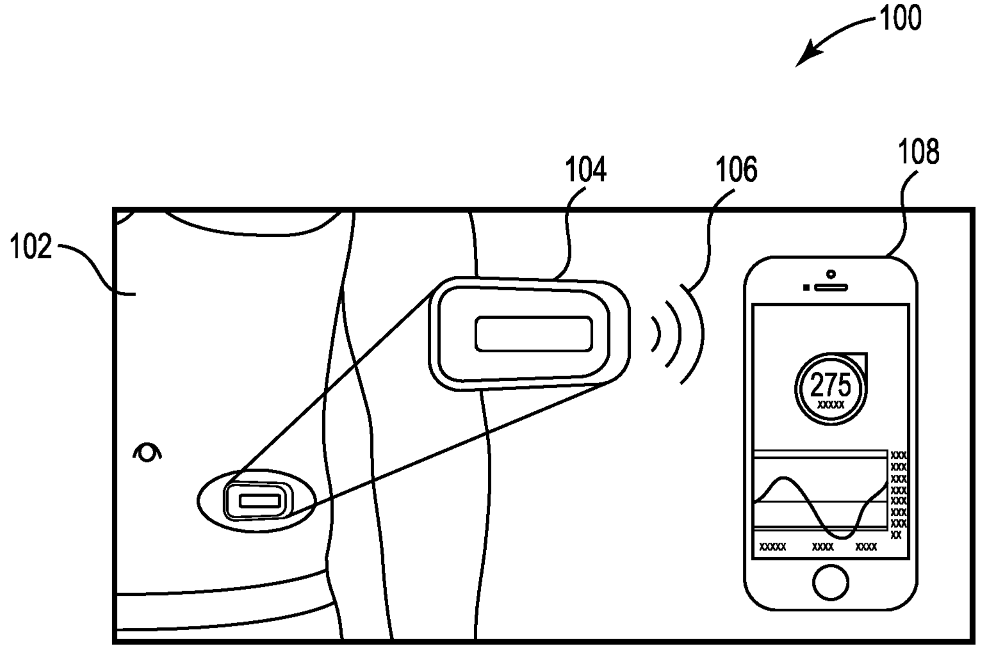
FIG. 1 is a diagram illustrating a continuous glucose monitoring (CGM) system according to an example.

Some examples disclosed herein are directed to a system of continuous electrochemical measurement. In some examples, the system of continuous electrochemical measurement is a CGM system. FIG. 1 is a diagram illustrating a CGM system 100 according to an example. The system 100 includes a CGM device 104 to be positioned on the body of a user 102 and wirelessly transmit CGM data to a host device 108 as indicated at 106. In the illustrated example, the host device 108 is a portable electronic device, such as a cellular telephone (e.g., smartphone). The CGM device 104 includes a transducer that is sensitive to the concentration of glucose of the user 102, and continuously reports the concentration of glucose to the host device 108 via wireless communications. In an example, the CGM device 104 includes a single electronic chip. The system 100 allows timely detection of a critical condition of the user 102, as evidenced by an unacceptable concentration of glucose.

In other examples, the host device 108 may be a tablet, personal digital assistant (PDA), laptop computer, watch or other wearable device, or other suitable computing device. Host device 108 may include a processor, memory, and a graphical user interface (GUI). The processor of the host device 108 may be any suitable programmable device that accepts digital data as input, is configured to process the input according to instructions or algorithms, and provides results as outputs. Digital data, the instructions or algorithms, or other intermediary instructions or data can be stored in the memory of host device 108. Outputs from the processor can be provided on the GUI. By placement of the host device 108 in the proximity of the CGM device 104, CGM data can be read and evaluated from the CGM device 104 by the host device 108, and/or data can be transmitted from the CGM device 104 to the host device 108. Software, such as mobile apps, can be utilized by host device 108 to store, archive, evaluate, compare, and/or display the sensed data.

Figure 2:
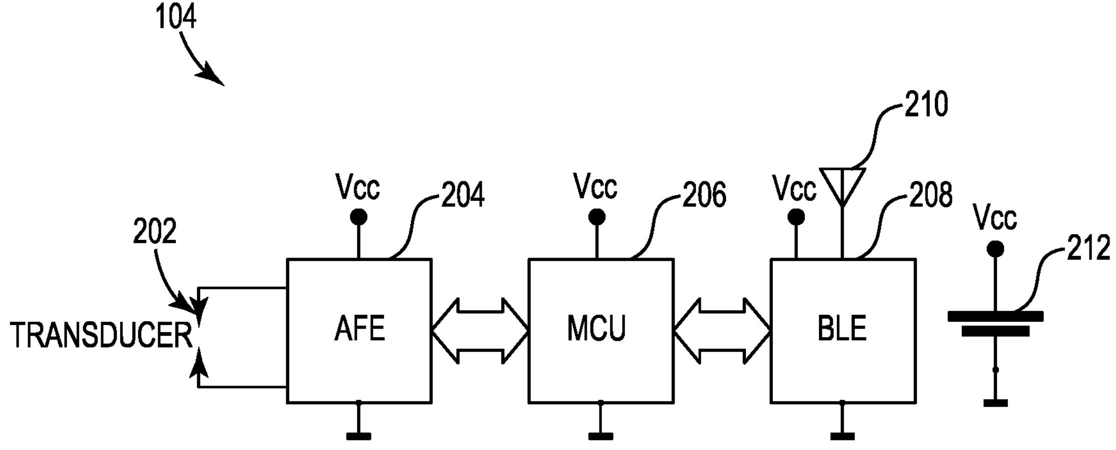
FIG. 2 is a diagram illustrating elements of the CGM device shown in FIG. 1 according to an example.

FIG. 2 is a diagram illustrating elements of the CGM device 104 shown in FIG. 1 according to an example. As shown in FIG. 2, CGM device 104 includes transducer 202, analog front-end (AFE) 204, microcontroller unit (MCU) 206, Bluetooth low-energy (BLE) radio 208 with antenna 210, and battery 212. In an example, transducer 202 is an electrochemical transducer, such as a glucose transducer. A bias voltage, Vbias, is applied to the transducer 202, and the transducer 202 converts glucose concentration to a corresponding analog current signal. The magnitude of the current is indicative of the glucose concentration. In other examples, transducer 202 may be configured to sense, detect, monitor, or otherwise measure biological, chemical, electrical, or other parameters or characteristics adjacent to, surrounding, or coupled to transducer 202. In some examples, a wireless communication protocol other than BLE may be used by radio 208, such as WI-FI, ZigBee, or other short-range, low-power communication protocol.

The AFE 204 converts the analog current signal from the transducer 202 to digital data. The MCU 206 controls the operation of device 104 and processes the digital data provided by AFE 204. BLE radio 208 wirelessly communicates with the host device 108 (FIG. 1). The AFE 204, MCU 206, and BLE radio 208 are powered by the battery 212 via a voltage, Vcc.

AFE 204, MCU 206, and BLE radio 208 may be implemented as an integrated circuit (IC) that includes a microprocessor or core. The processor may be any suitable programmable device that accepts digital data as input, is configured to process the input according to instructions or algorithms, and provides results as outputs. The processor may be configured to perform selected arithmetical, logical, and input/output operations. In an example, the processor may be a central processing unit (CPU) configured to carry out the instructions of a computer program. In other examples, the processor may be an embedded microprocessor. In some examples, the IC may include an application-specific integrated circuit (ASIC).

The IC implementing AFE 204, MCU 206, and BLE radio 208 may further include memory to provide non-transitory storage space. The memory may include volatile or non volatile memory as required by the coupled microprocessor or core to not only provide space to execute the instructions or algorithms, but also to provide the space to store the instructions themselves. The memory can further include space to store data collected by transducer 202. Volatile memory may include random access memory (RAM), dynamic random access memory (DRAM), or static random access memory (SRAM), for example. Non-volatile memory may include read-only memory (ROM), flash memory, ferroelectric RAM, hard disk, floppy disk, magnetic tape, or optical disc storage, for example. The foregoing examples in no way limit the type of memory that can be used, as these are given only by way of example and are not intended to limit subject matter hereof. These are examples of non-transitory computer readable storage media. The memory is non-transitory in the sense that it does not encompass a transitory signal but instead is made up of at least one memory component to store machine executable instructions for performing techniques described herein.

For a continuous glucose monitoring application, for example, the transducer 202 may generate a small current in the range of 1-20 nA at a bias voltage in the range of 150-600 mV. The use of this transducer 202 for continuous glucose measurement may involve a low-power receptor (i.e., AFE 204, MCU 206, and BLE radio 208) to provide long-term operation. The largest contribution to power consumption in such a system may be made by the AFE 204. The channel for measuring this low current may contain precision operational amplifiers (e.g., low bias voltage and leakage current). Leakage current may not be a big problem and may not increase power consumption. However, low-offset amplifiers may be large and too high-power for some applications. Examples disclosed herein are directed to a measuring channel (e.g., AFE 204) that makes measurement results insensitive to the offset voltage of the amplifiers, which in turn allows the use of low-power amplifiers.

Figure 3:
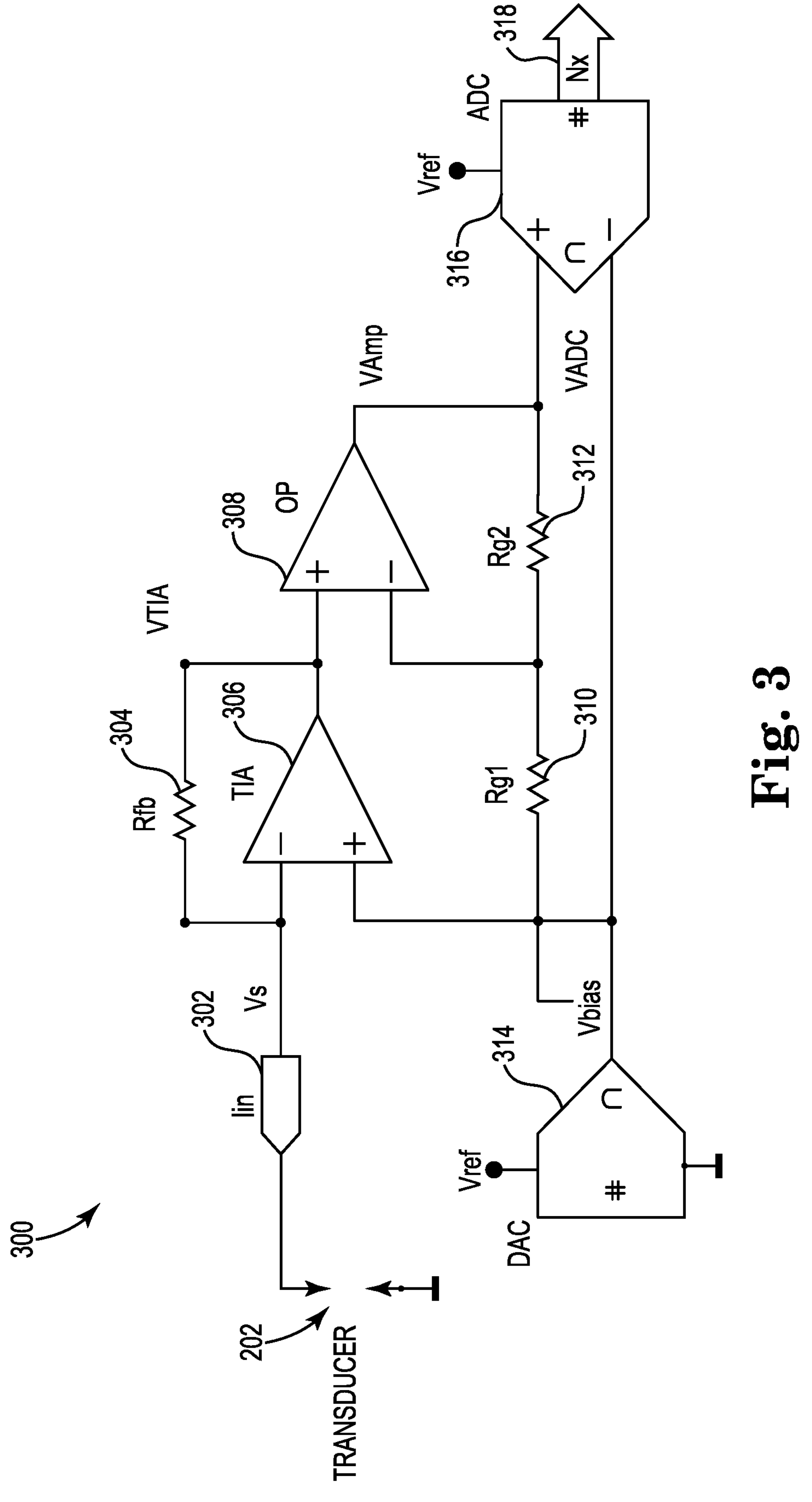
FIG. 3 is a diagram illustrating elements of an analog front-end (AFE) according to an example.

FIG. 3 is a diagram illustrating elements of an AFE 300 according to an example. AFE 300 is an example implementation of AFE 204 (FIG. 2). AFE 300 includes current (In) 302, resistor (Rfb) 304, transimpedance amplifier (TIA) 306, operational amplifier (OP) 308, resistor (Rg1) 310, resistor (Rg2) 312, digital to analog converter (DAC) 314, and analog to digital converter (ADC) 316.

The TIA 306 is biased with a Vbias voltage provided by the DAC 314. The voltage, $V_s$, applied to the transducer 202 is given in the following Equation (1):

$$V_s = Vbias + E_{TIA} \tag{1}$$

where:

Vbias=sensor bias voltage formed by the DAC 314;

$E_{TIA}$=offset voltage of TIA 306.

The voltage, $V_s$, causes the transducer current, Is(W), which depends on the glucose concentration, W. As a result, a voltage, $V_{TIA}$, is formed at the output of the TIA 306, which can be written as shown in the following Equation (2):

$$V_{TIA} = Vbias + E_{TIA} + Is(W) \cdot Rfb \tag{2}$$

where:

Is (W)=the transducer current; and

Rfb=resistor value of TIA feedback resistor 304.

Output voltage amplification of TIA 306 is provided by non-inverting operational amplifier 308. An issue is that amplification of the output voltage of the TIA 306 increases the voltage generated by the transducer current as well as the bias voltage. The bias voltage may be removed from the amplification by using the non-inverting operational amplifier 308 as a pseudodifferential amplifier by connecting the feedback resistor (Rg1) 310 to the bias voltage source (i.e., the output of the DAC 314). Thus, the bias voltage source plays the role of virtual ground. Therefore, the voltage, VAmp, at the output of the operational amplifier 308 is given by the following Equation (3):

$$V_{Amp} = (Is(W) \cdot Rfb + E_{TIA} + E_{OP}) \cdot \frac{Rg1 + Rg2}{Rg1} + Vbias \tag{3}$$

where:

$E_{OP}$=the offset voltage of the operational amplifier 308;

Rg1=resistance value of feedback resistor 310; and

Rg2=resistance value of feedback resistor 312.

Thus, the transducer signal is amplified relative to the virtual ground or the bias voltage. The bias voltage is eliminated from the transfer function by differential ADC 316, which has a positive input connected to the output of the operational amplifier 308, and a negative input connected to the output of the bias voltage source (i.e., output of DAC 314). Therefore, the voltage, $V_{ADC}$, at the differential input of the ADC 316 is given by the following Equation (4):

$$V_{ADC} = (Is(W) \cdot Rfb + E_{TIA} + E_{OP}) \cdot \frac{Rg1 + Rg2}{Rg1} \tag{4}$$

In this way, the ADC 316 converts only the signal of the transducer 202 distorted by offsets. This scheme allows using several different electrochemical techniques, such as sweep voltammetry, pulsed voltammetry, etc. The result of conversion of the transducer signal to a digital code 318 (Nx), can be written as shown in the following Equation (5):

$$Nx = K \cdot \left\{ (Is(W) \cdot Rfb + E_{TIA} + E_{OP}) \cdot \frac{Rg1 + Rg2}{Rg1} + E_{ADC} \right\} \tag{5}$$

where:

$E_{ADC}$=the offset voltage of the ADC 316;

K=the conversion factor of the ADC 316.

Two factors can decrease performance of AFE 300. First, the transducer 202 may not be a resistor whose value depends on the analyte (e.g., glucose) concentration. Electrochemical effects, such as a double-layer capacitance, may make the transducer 202 a complex circuit containing big capacitances. Second, the output impedance at a high-frequency of the low-power active components may be large. This can create an unexpected positive feedback loop that may cause oscillation or unwanted voltage spikes under dynamic loads, such as those formed by an ADC sample capacitor.

Figure 4:
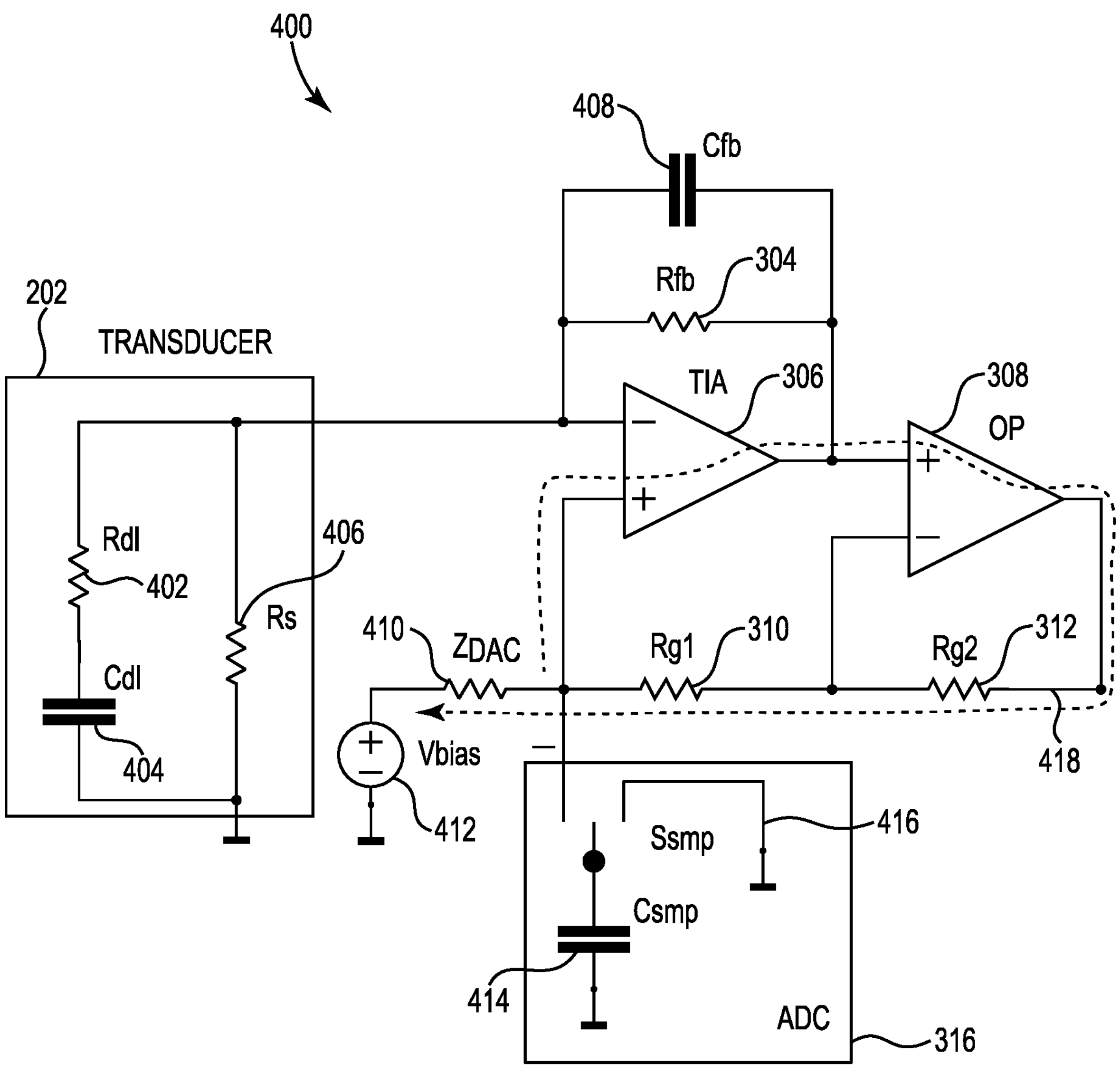
FIG. 4 is a diagram illustrating an equivalent circuit for the AFE shown in FIG. 3 according to an example.

The factors mentioned above are described in further detail below with reference to FIG. 4. FIG. 4 is a diagram illustrating an equivalent circuit 400 for the AFE 300 shown in FIG. 3 according to an example. The transducer 202 is represented by a simplified equivalent circuit containing one double-layer capacitor (Cdl) 404 and its series resistance (Rdl) 402. The value of this capacitor 404 may be large. The value of the capacitance of capacitor 404 depends on the size of the electrodes of transducer 202, and in continuous glucose monitoring applications, it may be in the range of a hundred nano-farads. A feedback capacitor (Cfb) 408 in parallel with the feedback resistor 304 may be used to compensate the increase of the gain of TIA 306 at high frequency caused by the transducer capacitance 404.

The DAC 314 (FIG. 3) is represented in FIG. 4 as the bias voltage source (Vbias) 412 in series with the DAC output impedance ($Z_{DAC}$) 410. The positive feedback loop formed by this impedance is shown by the dotted line 418. The risk of oscillation increases if the transducer capacitance 404 is not completely compensated by the feedback capacitor 408 due to a limiting of the value of this capacitor 408 to prevent the TIA 306 self-oscillation.

The ADC 316 (FIG. 3) is represented in FIG. 4 as including a sampling capacitor (Csmp) 414 and a sampling element (Ssmp) 416. An additional initiator of the DAC voltage variation can be the sampling capacitor 414 of the ADC 316. This capacitor 414 connecting to the DAC output causes a rapid change in its voltage followed by charging the sampling capacitor 414 through the DAC impedance.

Figure 5:
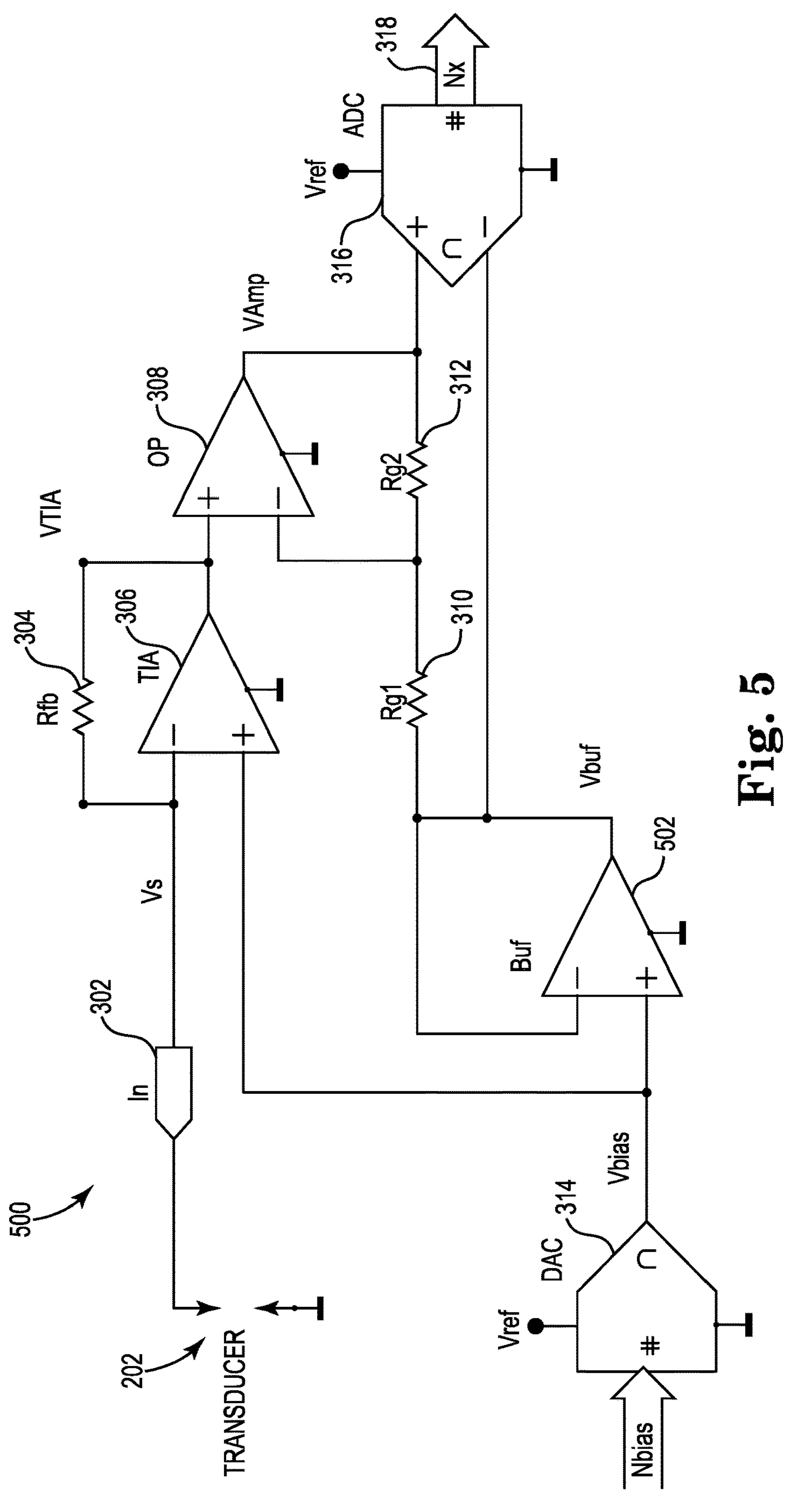
FIG. 5 is a diagram illustrating elements of an AFE according to another example.

To address issues described above, an additional buffer may be added between the TIA 306 and amplifier 308 connections to the DAC 314 output as shown in FIG. 5. FIG. 5 is a diagram illustrating elements of an analog front-end (AFE) 500 according to another example. In the illustrated example, AFE 500 includes the same elements as AFE 300 (FIG. 3), and includes an additional buffer 502. This buffer 502 decouples the input of the TIA 306 from the output of the amplifier 308 and breaks the positive feedback loop. Additionally, the ADC sampling does not impact the TIA 306.

The output voltage, $V_{buf}$, of buffer 502 is given in the following Equation (6):

$$V_{buf} = Vbias + E_{buf} \tag{6}$$

where:

$E_{buf}$=the offset voltage of the buffer 502;

The conversion result is given in the following Equation (7):

$$N = K \cdot \left\{ (Is(W) \cdot Rfb + E_{TIA} + E_{OP}) \cdot \frac{Rg1 + Rg2}{Rg1} - E_{buf} \cdot \frac{Rg2}{Rg1} + E_{ADC} \right\} \tag{7}$$

The differential ADC 316 measurement removes Vbias and buffer error. As was mentioned above, the transducer current for continuous glucose monitoring may be in the range of 1-20 nA. If the value of the feedback resistor 304 of the TIA 306 is 1 MOhm, the informative voltage on the output of the TIA 306 is 1-20 mV. For an error of the concentration measurement less than 1 mg/dL, the total offset is to be less than 20 uV, or for each operational amplifier 308, the offset is to be less than 10 uV. A small offset may be a challenge for small and low-power operational amplifiers.

The offset issue can be addressed with a modulation-demodulation method for the informative parameter when the non-informative parameter remains constant. For this purpose, a switch may be added that shorts the feedback resistor 304 of the TIA 306 as shown in FIG. 6.

Figure 6:
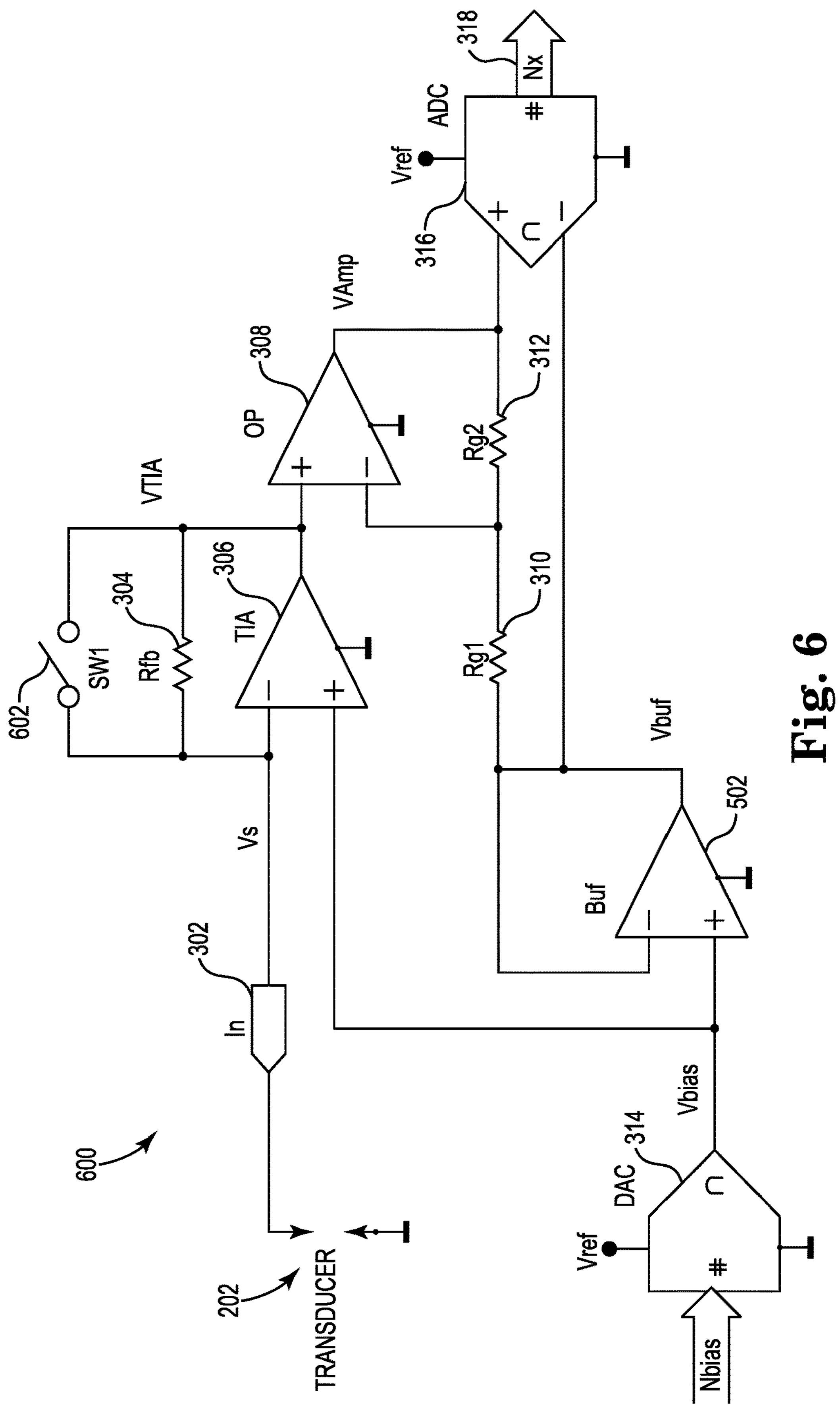
FIG. 6 is a diagram illustrating elements of an AFE according to another example.

FIG. 6 is a diagram illustrating elements of an analog front-end (AFE) 600 according to another example. In the illustrated example, AFE 600 includes the same elements as AFE 500 (FIG. 5), and includes an additional switch (SW1) 602. The output of the ADC 316 when the switch 602 is opened is defined in Equation (7). When the switch 602 is closed, the value of the feedback resistor 304 of the TIA 306 becomes equal to the switch resistance $r_{sw}$. The output of the ADC 316 in this configuration is given in the following Equation (8):

$$N(r_{sw}) = K \cdot \left\{ (Is(W) \cdot r_{sw} + E_{TIA} + E_{OP}) \cdot \frac{Rg1 + Rg2}{Rg1} - E_{buf} \cdot \frac{Rg2}{Rg1} + E_{ADC} \right\} \tag{8}$$

Having these two values, for conditions when the switch 602 is open and when the switch 602 is closed, we can find the difference of these values as shown in the following Equation (9):

$$Nx = N(Rfb) - N(r_{sw}) = K \cdot Is(W) \cdot (Rfb - r_{sw}) \cdot \frac{Rg1 + Rg2}{Rg1} \tag{9}$$

The closed switch resistance is designated by design in a range. Assume, for example, that switch 602 has a resistance at the closed condition of 100 Ohm±30%. The error introduced by this variation is given in the following Equation (10):

$$\delta Nr_{sw} = \frac{r_{sw} \cdot \delta r_{sw}}{Rfb} = \frac{30 \text{ Ohm}}{1 \text{ MOhm}} = 0.003\% \quad (10)$$

This error is so small that it can be ignored even if $r_{sw}=0$ is used.

Figure 7:
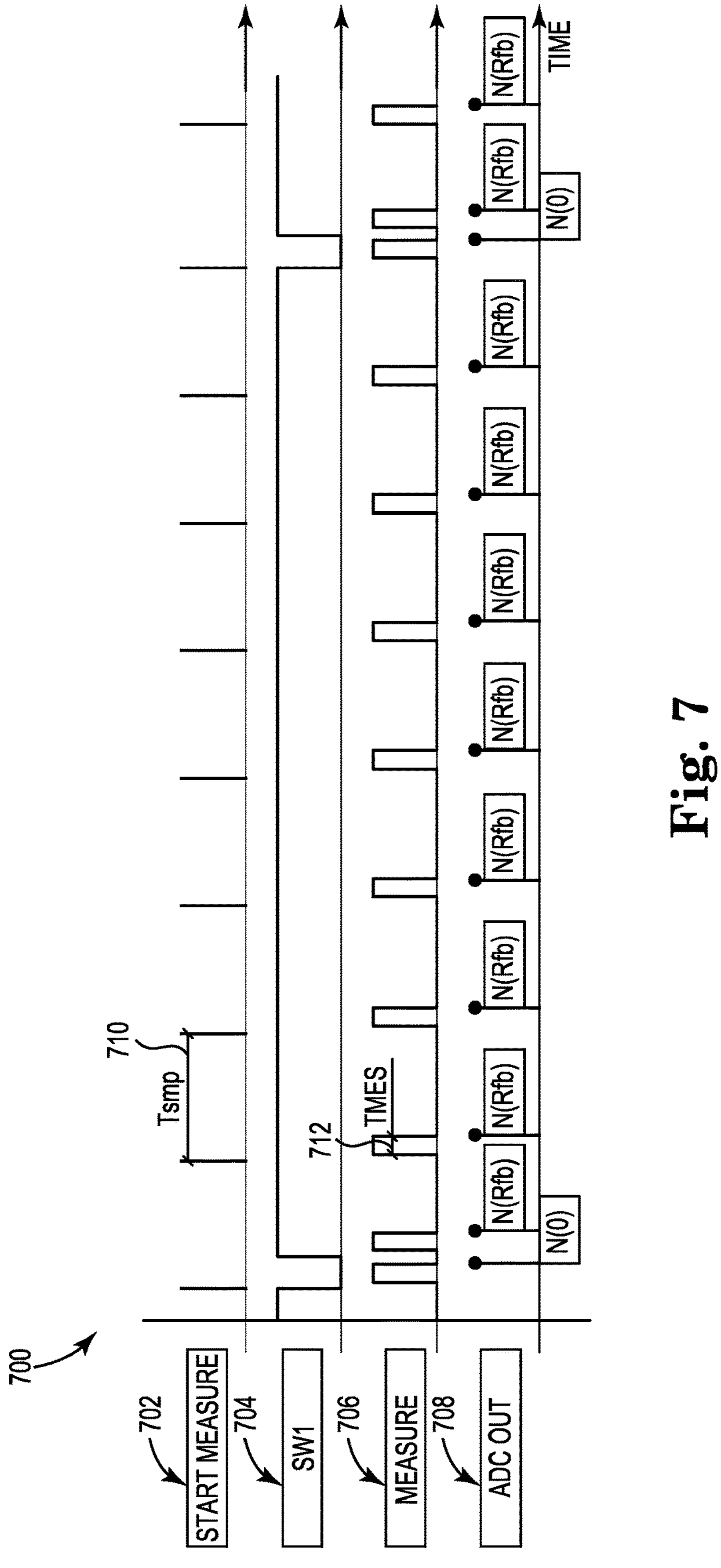
FIG. 7 is a diagram illustrating a graph of signals of the AFE shown in FIG. 6 according to an example.

FIG. 7 is a diagram illustrating a graph 700 of signals of the AFE 600 shown in FIG. 6 according to an example. The signals include a Start Measure signal 702, an SW1 signal 704, a Measure signal 706, and an ADC Out signal 708. A controller (e.g., MCU 206 shown in FIG. 2) initiates measurements by generating Start Measure signal 702, and configuring the AFE 600 including the switch 602 (i.e., open/close conditions). The SW1 signal 704 controls the switch 602, with a low value of the signal 704 indicating that the switch 602 is closed, and a high value of the signal 704 indicating that the switch 602 is open.

The "Start Measure" signal is generated periodically after each Tsmp period 710 and initiates the ADC conversion sequence. The conversion runs during Tmes time periods 712 and results in an output of the ADC 316 as indicated by signal 708. The first measure runs with the switch 602 closed, giving a result, N(0), from signal 708. After the switch 602 is opened, as indicated by a high value for signal 704, and after a period of time that is sufficient for settling of the active component, the next conversion gives a result, N(Rfb)[1], from signal 708. The MCU 206 calculates the difference N(Rfb)[1]-N(0), and uses the difference to calculate a glucose concentration value. After the next Tsmp period 710, whose duration can take up to minute in some examples, the next conversion is started giving a result, N(Rfb)[2]-N(0), and a new value of the glucose concentration is calculated. This operation repeats M times. After that, the sequence starting with the closing of switch 602 is repeated cyclically. The dynamic alternation of the switch 602 compensates for the offset error of the TIA 306.

Examples disclosed herein form at the ADC 316 an input signal that is proportional to the transducer current without the receptor bias even if it changes. In some examples, the method of the measured current modulation by modulation of the gain of the TIA 306 eliminates the necessity to use precise operational amplifiers with small offsets due to invariance of the result of conversion to the offset values.

An example of the present disclosure is directed to a continuous electrochemical monitoring device. FIG. 8 is a block diagram illustrating a continuous electrochemical monitoring device 800 according to an example. The device 800 includes an electrochemical transducer 802 to continually generate a signal indicative of a characteristic of a user. The device 800 includes a transimpedance amplifier 804 to receive the signal from the transducer at a first input, receive a bias voltage at a second input, and generate an output voltage. The device 800 includes an operational amplifier 806 to receive the output voltage at a first input, and output an amplified output voltage. The device 800 includes a differential analog to digital converter 808 to receive the amplified output voltage at a first input, receive the bias voltage at a second input, and continually generate a digital output indicative of the characteristic of the user.

The electrochemical transducer 802 may be a glucose transducer positioned on a body of the user, and the characteristic may be a glucose concentration of the user. The device 800 may further include a microcontroller unit to receive the digital output from the differential analog to digital converter and cause glucose concentration data to be wirelessly transmitted to a host device. The device 800 may further include a digital to analog converter to generate the bias voltage. The device 800 may further include a first resistor coupled between an output of the operational amplifier 806, and a second input of the operational amplifier 806. The device 800 may further include a second resistor coupled between the second input of the operational amplifier 806 and a source of the bias voltage. The device 800 may further include a buffer having a first input coupled to an output of the digital to analog converter to receive the bias voltage, and an output coupled to the second input of the differential analog to digital converter 808. The output of the buffer may also be coupled to a second input of the buffer and to the second resistor.

The device 800 may further include a feedback resistor coupled between an output of the transimpedance amplifier 804 and the first input of the transimpedance amplifier 804; and a switch coupled in parallel with the feedback resistor between the output of the transimpedance amplifier 804 and the first input of the transimpedance amplifier 804. The switch may be controlled to open and close to compensate for an offset error of the transimpedance amplifier. A digital value output by the differential analog to digital converter while the switch is closed may be subtracted from subsequent digital values output by the differential analog to digital converter 808 while the switch is open.

The electrochemical transducer 802 may generate currents in a range of 0-20 nA. The bias voltage in device 800 may in a range of 150-600 mV.

Figure 9:
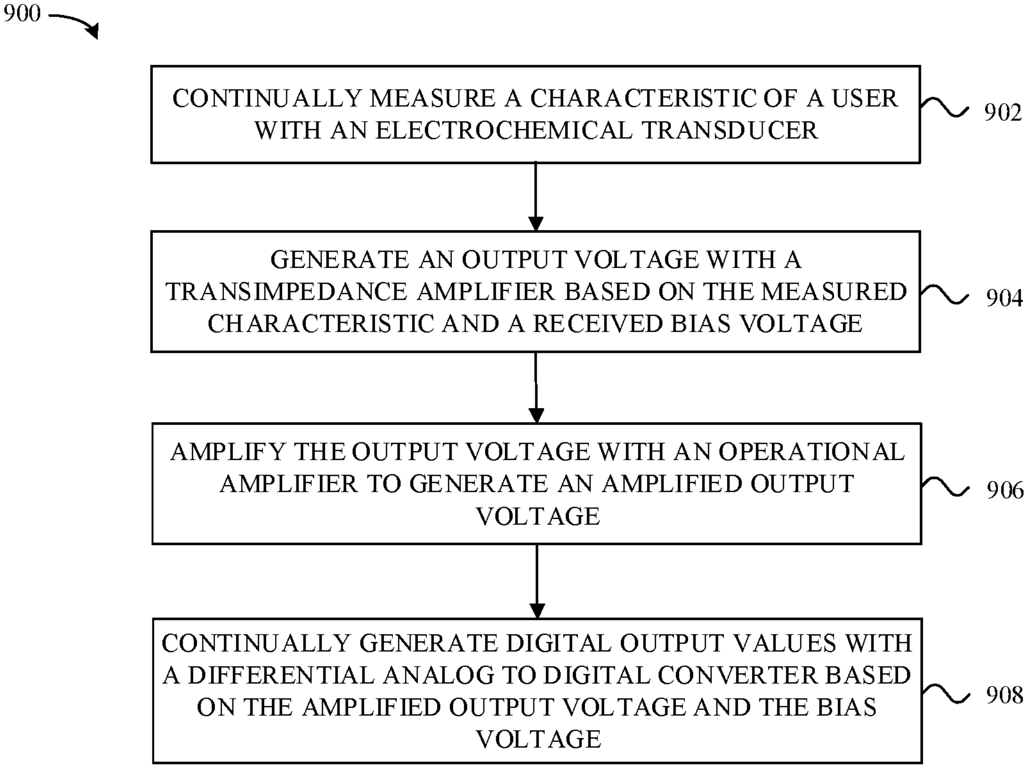
FIG. 9 is a flow diagram illustrating a method of continuous electrochemical monitoring according to an example.

Another example of the present disclosure is directed to a method of continuous electrochemical monitoring. FIG. 9 is a flow diagram illustrating a method 900 of continuous electrochemical monitoring according to an example. Method 900 includes, at 902, continually measuring a characteristic of a user with an electrochemical transducer. Method 900 includes, at 904, generating an output voltage with a transimpedance amplifier based on the measured characteristic and a received bias voltage. Method 900 includes, at 906, amplifying the output voltage with an operational amplifier to generate an amplified output voltage. Method 900 includes, at 908, continually generating digital output values with a differential analog to digital converter based on the amplified output voltage and the bias voltage.

In an example of method 900, the electrochemical transducer may be a glucose transducer positioned on a body of the user, and the characteristic may be a glucose concentration of the user. The method 900 may further include receiving the digital output values with a microcontroller unit; and wirelessly transmitting glucose concentration data based on the digital output values to a host device.

The method 900 may further include providing a feedback resistor coupled between an output of the transimpedance amplifier and a first input of the transimpedance amplifier that receives the measured characteristic; and providing a switch coupled in parallel with the feedback resistor between the output of the transimpedance amplifier and the first input of the transimpedance amplifier. The method 900 may further include controlling the switch to open and close to compensate for an offset error of the transimpedance amplifier.

Another example of the present disclosure is directed to a continuous glucose monitoring device. FIG. 10 is a block diagram illustrating a continuous glucose monitoring device 1000 according to an example. Device 1000 includes a glucose transducer 1002 to continually generate a signal indicative of a glucose concentration of a user. Device 1000 includes a transimpedance amplifier 1004 to receive the signal from the transducer 1002 at a first input, receive a bias voltage at a second input, and generate an output voltage. Device 1000 includes an operational amplifier 1006 to receive the output voltage at a first input, and output an amplified output voltage. Device 1000 includes an analog to digital converter 1008 to receive the amplified output voltage at a first input, receive the bias voltage at a second input, and continually generate digital output values based on a difference between the amplified output voltage and the bias voltage. Device 1000 includes a microcontroller unit 1010 to receive the digital output values from the analog to digital converter 1008 and cause glucose concentration data to be wirelessly transmitted to a host device.

In an example of device 1000, the glucose transducer 1002 may generate currents in a range of 0-20 nA, and the bias voltage may be in a range of 150-600 mV.

It is to be understood that the features of the various exemplary embodiments described herein may be combined with each other, unless specifically noted otherwise.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A continuous electrochemical monitoring device, comprising:

an electrochemical transducer to continually generate a signal indicative of a characteristic of a user;

a transimpedance amplifier to receive the signal from the transducer at a first input, receive a bias voltage at a second input, and generate an output voltage;

an operational amplifier to receive the output voltage at a first input, and output an amplified output voltage;

a differential analog to digital converter to receive the amplified output voltage at a first input, receive the bias voltage at a second input, and continually generate a digital output indicative of the characteristic of the user;

a feedback resistor coupled between an output of the transimpedance amplifier and the first input of the transimpedance amplifier; and a switch coupled in parallel with the feedback resistor between the output of the transimpedance amplifier and the first input of the transimpedance amplifier.

2. The continuous electrochemical monitoring device of claim 1, wherein the electrochemical transducer is a glucose transducer positioned on a body of the user, and wherein the characteristic is a glucose concentration of the user.

3. The continuous electrochemical monitoring device of claim 2, and further comprising:

a microcontroller unit to receive the digital output from the differential analog to digital converter and cause glucose concentration data to be wirelessly transmitted to a host device.

4. The continuous electrochemical monitoring device of claim 1, and further comprising:

a digital to analog converter to generate the bias voltage.

5. The continuous electrochemical monitoring device of claim 4, and further comprising:

a first resistor coupled between an output of the operational amplifier, and a second input of the operational amplifier.

6. The continuous electrochemical monitoring device of claim 5, and further comprising:

a second resistor coupled between the second input of the operational amplifier and a source of the bias voltage.

7. The continuous electrochemical monitoring device of claim 6, and further comprising:

a buffer having a first input coupled to an output of the digital to analog converter to receive the bias voltage, and an output coupled to the second input of the differential analog to digital converter.

8. The continuous electrochemical monitoring device of claim 7, wherein the output of the buffer is also coupled to a second input of the buffer and to the second resistor.

9. The continuous electrochemical monitoring device of claim 1, wherein the switch is controlled to open and close to compensate for an offset error of the transimpedance amplifier.

10. The continuous electrochemical monitoring device of claim 9, wherein a digital value output by the differential analog to digital converter while the switch is closed is subtracted from subsequent digital values output by the differential analog to digital converter while the switch is open.

11. The continuous electrochemical monitoring device of claim 1, wherein the electrochemical transducer generates currents in a range of 0-20 nA.

12. The continuous electrochemical monitoring device of claim 9, wherein the bias voltage is in a range of 150-600 mV.

13. The continuous electrochemical monitoring device of claim 1, wherein the switch is directly coupled between the output of the transimpedance amplifier and the first input of the transimpedance amplifier.

14. A method, comprising:

continually measuring a characteristic of a user with an electrochemical transducer;

generating an output voltage with a transimpedance amplifier based on the measured characteristic and a received bias voltage;

amplifying the output voltage with an operational amplifier to generate an amplified output voltage;

continually generating digital output values with a differential analog to digital converter based on the amplified output voltage and the bias voltage;

providing a feedback resistor coupled between an output of the transimpedance amplifier and a first input of the transimpedance amplifier that receives the measured characteristic; and providing a switch coupled in parallel with the feedback resistor between the output of the transimpedance amplifier and the first input of the transimpedance amplifier.

15. The method of claim 14, wherein the electrochemical transducer is a glucose transducer positioned on a body of the user, and wherein the characteristic is a glucose concentration of the user.

16. The method of claim 15, and further comprising:

receiving the digital output values with a microcontroller unit; and wirelessly transmitting glucose concentration data based on the digital output values to a host device.

17. The method of claim 14, and further comprising:

controlling the switch to open and close to compensate for an offset error of the transimpedance amplifier.

18. The method of claim 14, wherein providing the switch comprises providing the switch directly coupled between the output of the transimpedance amplifier and the first input of the transimpedance amplifier.

19. A continuous glucose monitoring device, comprising:

a glucose transducer to continually generate a signal indicative of a glucose concentration of a user;

a transimpedance amplifier to receive the signal from the transducer at a first input, receive a bias voltage at a second input, and generate an output voltage;

an operational amplifier to receive the output voltage at a first input, and output an amplified output voltage;

an analog to digital converter to receive the amplified output voltage at a first input, receive the bias voltage at a second input, and continually generate digital output values based on a difference between the amplified output voltage and the bias voltage; and a microcontroller unit to receive the digital output values from the analog to digital converter and cause glucose concentration data to be wirelessly transmitted to a host device;

a feedback resistor coupled between an output of the transimpedance amplifier and the first input of the transimpedance amplifier; and a switch coupled in parallel with the feedback resistor between the output of the transimpedance amplifier and the first input of the transimpedance amplifier.

20. The continuous glucose monitoring system of claim 19, wherein the glucose transducer generates currents in a range of 0-20 nA, and wherein the bias voltage is in a range of 150-600 mV.

* * * * *